United States Patent [19]

Poppe et al.

[11] Patent Number: 4,476,149
[45] Date of Patent: Oct. 9, 1984

[54] PROCESS FOR THE PRODUCTION OF AN ANALYSIS TEST STRIP

[75] Inventors: Werner Poppe, Bobenheim-Roxheim; Rainer van Rijekevorsel, Brühl; Uwe Ruppender; Heinz Macho, both of Mannheim, all of Fed. Rep. of Germany

[73] Assignee: Boehringer Mannheim GmbH, Mannheim, Fed. Rep. of Germany

[21] Appl. No.: 406,678

[22] Filed: Aug. 9, 1982

[30] Foreign Application Priority Data

Aug. 27, 1981 [DE] Fed. Rep. of Germany ....... 3133826

[51] Int. Cl.³ .................... G01N 33/52; G01N 35/00
[52] U.S. Cl. ........................................ 427/2; 101/223;
  101/243; 235/375; 235/462; 422/56; 422/67
[58] Field of Search .................... 422/56, 57, 58, 55,
  422/67; 427/2; 235/462, 463, 375; 101/223,
  224, 243, 244, 281, 288

[56] References Cited

U.S. PATENT DOCUMENTS

| | | | |
|---|---|---|---|
| 3,127,281 | 3/1964 | Meyer | 427/2 |
| 3,648,604 | 3/1972 | Warsager | 101/244 X |
| 3,712,210 | 1/1973 | Landis | 101/332 X |
| 3,901,148 | 8/1975 | Clark | 101/243 X |
| 3,907,503 | 9/1975 | Betts et al. | 422/67 |
| 3,920,957 | 11/1975 | Sims | 235/462 X |
| 3,926,110 | 12/1975 | Hubbard et al. | 101/288 X |
| 3,933,094 | 1/1976 | Murphy et al. | 235/491 X |
| 4,056,361 | 11/1977 | Peters et al. | 422/64 |
| 4,087,332 | 5/1978 | Hansen | 422/56 X |
| 4,121,574 | 10/1978 | Lester | 235/462 X |
| 4,260,392 | 4/1981 | Lee | 422/56 X |

Primary Examiner—Arnold Turk
Attorney, Agent, or Firm—Sprung Horn Kramer & Woods

[57] ABSTRACT

An analysis test strip and a process for the production of analysis test strips with a longitudinal carrier upon which is fixed at least one test field. The test field material is produced batchwise in an amount sufficient for a plurality of test strips, and thereafter, in a chronologically separate working step, is continuously fixed in the form of at least one band onto a parallel-running substantially wider band of test strip carrier material. The band as a whole is cut up transversely to its longitudinal direction into a plurality of test strips. Prior to the cutting up, a bar code is applied to the carrier band running parallel to the edges thereof of such high information density that it is suitable as a store of batch-specific information necessary for the quantitative evaluation of the reaction which has previously been obtained by investigation of the test field material of one batch.

9 Claims, 6 Drawing Figures

PROCESS FOR THE PRODUCTION OF AN ANALYSIS TEST STRIP

BACKGROUND OF THE INVENTION

The present invention is concerned with test strips and with a process for the production thereof.

More particularly, the present invention is concerned with a process for the production of an analysis strip with a longitudinal carrier upon which is fixed at least one test field, in which the test field material is produced batchwise in an amount sufficient for a plurality of test strips and thereafter, in a chronologically separated working step, is continuously fixed in the form of a band onto a parallel-running, substantially wider band of test strip band finally being divided transversely to its longitudinal direction into a plurality of test strips. Furthermore, the present invention is directed to a test strip for the analysis of components of a liquid, especially of a human body fluid, with a longitudinal carrier with a front end and a rear end, close to the front end there being applied at least one test field for an analysis and close to the rear end a holding region is provided in order to facilitate moistening the test strip with a liquid and carrying out of the evaluation, the test strip also being provided with a mechanically readable coding in the form of lines running substantially transversely to the test strip.

In recent years, analytical determinations, especially for medical purposes, have been carried out to an increasing extent with the help of test strips. The handling of these test strips is very simple. Urine test strips are generally briefly dipped into a sample and the liquid subsequently simply allowed to drip off. For blood investigations, a drop of blood is usually applied and again wiped off after it has fully soaked into the test field. However, other methods are also possible. In the case of the conventional test strips, on the test fields there takes place a chemical reaction between component materials of the body fluid and reagents present on the test field, which leads to a color change of the test field. In the initial period of analysis with test strips, the color change was evaluated visually.

The visual evaluation of the color change only permits a qualitative or semi-quantitative assessment of the concentration of the material to be analyzed. However, because of the simple handling and the favorable costs of the test strips for smaller series of investigations, already for quite a long time an endeavour has been made to quantitatively evaluate the color change with the help of appropriate apparatus. Usually, use is made of a reflection photometer which determines the degree of reflection of the test field surface, after the reaction has taken place, at one or more wavelengths.

A difficult problem in the case of these endeavours is caused by the fact that the test fields of the test strips, which usually consist of papers or fleeces impregnated with appropriate reagents and dried, cannot be so well reproducibly produced that they can then also be evaluated with the desired degree of exactitude if they originate from different production batches. Because of this, various suggestions have already been made to provide the evaluation device with typical, i.e. batch-specific, information for a particular production batch, especially the particular dependence of the concentration of the substance to be analyzed upon the particular degree of reflection. For example, for this purpose, interchangeable scales are employed which, in each case, are contained in the test strip packings and can be introduced into the appropriate apparatus in order to calibrate it for a particular batch. The necessary evaluation information can also be provided in mechanically readable form, for example as punched or magnetic cards in the packing. However, these methods suffer from considerable disadvantages. In particular, there is a great danger of confusion because the variable scales or punched cards must be changed by hand every time a new test strip packing is opened. If this is not done, then it results unavoidably in erroneous measurements which, especially in the field of medicine, can have serious results.

SUMMARY OF THE INVENTION

Therefore, the object of the present invention is to incorporate the amount of information necessary for a batch-specific evaluation (of the order of magnitude of at least about 50 bits) onto a test strip in such a manner that it is mechanically readable without problems for the evaluation apparatus and the apparatus can be easily operated. The appropriate production process is to be adapted to the previously used production processes for test strips and to be economical to carry out.

Thus, according to the present invention, there is provided a process for the production of an analysis test strip with a longitudinal carrier upon which is fixed at least one test field, the test field material being produced batchwise in an amount sufficient for a plurality of test strips, and thereafter, in a chronologically separate working step, is continuously fixed in the form of at least one band on to a parallel-running substantially wider band of test strip carrier material in a running through process and finally the band as a whole is cut up transversely to its longitudinal direction into a plurality of test strips, wherein onto the test strip carrier band, before the cutting up, there is applied a bar code, running parallel to the edges of the test strip carrier band, of such high information density that it is suitable as a store of batch-specific information necessary for the quantitative evaluation of the reaction which has previously been obtained by investigation of the test field material of one batch.

A series of difficult problems run counter to this initially simple appearing solution. There is first to be taken into account the fact that conventional test strips have very small dimensions (about 6 mm.×80 mm.). For various reasons, explained in the following in more detail, only a part thereof is available for the batch-specific coding, for example an area of about 30 mm.×6 mm. On the other hand, the amount of information necessary for a batch-specific coding, especially the giving of the calibration curve between reflection and concentration, is on the order of magnitude of at least about 50 bits. To these very limited place conditions are to be added difficult production-technical peripheral conditions. The test strips must be produced very quickly, dependably and economically. The application of the coding must thereby be adapted as far as possible to the proven processes for the production of test strips initially described in detail. Due to the application of coding to the test strips, the test field material must not be influenced in such a manner that its previously measured properties, which, of course, lead to the batch-specific coding, again change during the application procedure. Because of these apparently insurmountable problems, it has obviously not been previously suggested to use a bar code of sufficiently high information density in the sense of the present invention, although it is known, for example, to use bar codings for the characterizing of foodstuff packages.

This clearly existing prejudice in the expert in the field thereby becomes especially clear in that recently test strips and an appropriate evaluation device have been described which are provided with a mechanically readable coding in the form of lines running substantially transversely to the test strips. However, this coding is only suitable for the identification of the particular type of test strip inserted into the apparatus (i.e. the nature of the analysis to be carried out) because, obviously due to the above-described production-technical problems, the information density is very low. The smallest breadth of the code lines and the distances between them is, in this case, more than 1 mm., whereas for the batch-specific coding according to the present invention, under the conditions given on conventional test strips, a maximum breadth of the smallest line of about 100 to 200 $\mu$m. is necessary. In the case of the known apparatus, the coding is read off with a light beam passing through the test strip. In contradistinction thereto, the bar code used according to the present invention is preferably evaluated by a reflection process since, in the scope of the present invention, we have found that the disturbances of the light beam in an approximately 300 $\mu$m. thick test strip makes very difficult a dependable reading of a bar code of such high information density in a transmission process.

The batch specific information necessary for the evaluation can be obtained after production of the test field material, thus usually of the test field paper impregnated with reagents and dried. Preferably, however, a band-shaped unit is first produced from the test field material and the test strip carrier, which corresponds completely to the finished test strip but is not yet cut up into the individual strips. From this band there can then be very simply obtained typical examples for a particular batch by cutting out several sample test strips in an appropriate manner. This process has the advantage that the sample test strips can be investigated with apparatus which are very similar to the apparatus employed for the subsequent analysis, i.e. the determination of the batch-specific properties takes place under especially realistic conditions. Furthermore, by means of this preferred process, it is possible to avoid any changes of the properties of the test field material due to the application to the test strip carrier band which would lead to a corresponding falsification of the measurement results.

The bar code can be applied in various ways to the test strip carrier band material. For example, one possible solution would be to print a paper strip with the particular code and then to stick it on parallel to the test field band at an appropriate place on the test strip carrier band. Instead of paper, an appropriate foil can also be used for this purpose. However, such processes are comparatively laborious. Therefore, especially preferably the bar code is applied with the help of a cylindrical roller directly onto the running carrier band, the carrier band thereby passing through and between the cylindrical roller and a printing device.

Such a process is, in principle, possible with the help of a conventional printing technique, i.e. by applying a liquid dyestuff to the test strip using a cylindrical roller provided with an appropriate embossment and then dried. However, such a printing process gives rise to considerable difficulties when, as is possibly necessary in the case of a large-scale production of test strips, code bars are to be clearly printed with a breadth of, for example, only 100 or 200 $\mu$m. at very small distances apart on to a carrier band of 100 to 200 m. length. It must thereby be remembered that the code bars, in order to be readable with certainty, must have edges which are as sharp as possible and must be positioned exactly not only with regard to one another but also with regard to their position on the test strips. This requirement is made even more severe in that even in the case of the use of the present invention, the safety code otherwise usual in the case of bar codings can only be used to a very limited extent due to a shortage of space. Therefore, especially high requirements are demanded of the quality of the application of the code bars.

These requirements are fulfilled by a preferred embodiment of the present invention in which not a liquid dye but rather a solid dye layer is transferred from a dye layer carrier film to the test strip carrier band with the use of pressure and possibly with heating. In this case, drying is unnecessary and an extremely precise coding can be applied over the whole length of the test strip carrier band usual in the case of the production of test strips. The dye layer itself can thereby be less than 1 $\mu$m. thick.

The so-called heat seal process is especially preferred for this purpose. In this case, on the dye layer carrier film there is usually present a layer of separation lacquer, thereupon the dye layer to be transferred and, on the very top, a layer of heat sealing agent, i.e. a polymer which liquefies upon heating and manifests an adhesive action. In this case, the application of the dye layer is carried out with the use of a heated cylindrical roller provided with an appropriate embossment which presses from behind against the dye layer carrier film, thereby causes the sealing agent to melt and transfers the dye layer with the separating lacquer on to the test strip carrier band. Heat seal foils suitable for this purpose are available, for example, from the firm L. Kurz, Fürth i. Bayern under the designations stamping foil "Alufin" or "Luxor".

Numerous materials are suitable for the application of the bar code. Especially preferred are the synthetic resin materials transferrable in solid form and especially by heat sealing, which contain pigments in an appropriate binding material. However, especially preferably, the code bars consist of a material which contains metallic components. Such bars are especially useful when infra-red light is used for the reading of the bar code. Thus, the synthetic resins usually employed as test strip carrier materials only reflect infra-red light relatively weakly, whereas metallic code bars act reflectingly. An especially good contrast is thereby given which increased the readability of the bar code. Finally, as a light source for the bar code reader, infra-red light diodes are especially well suited because, in the case f a given power requirement, they have an especially high light intensity.

The invention will now be explained in more detail in the following, with reference to the accompanying drawings, in which:

DETAILED DESCRIPTION OF THE INVENTION

Figure 1:
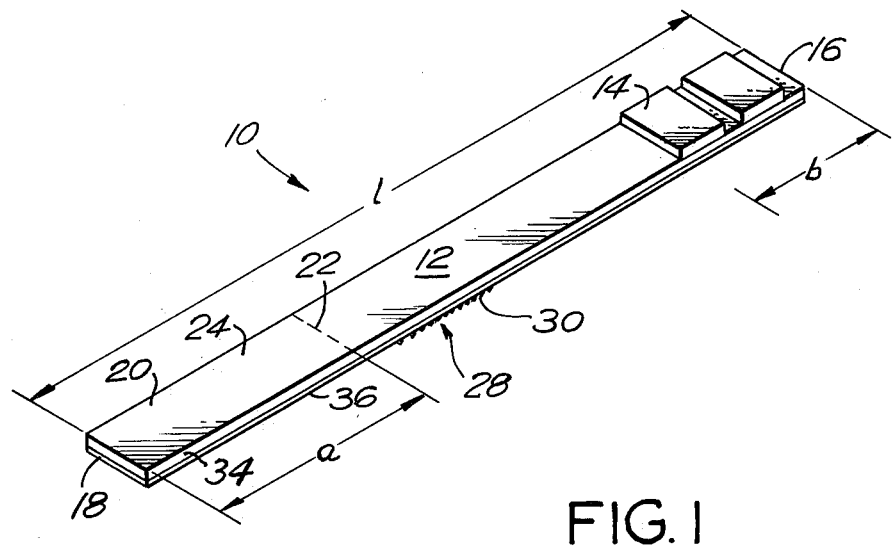
FIG. 1 is a schematic perspective view of a test strip according to the present invention, seen obliquely from above.
Figure 2:
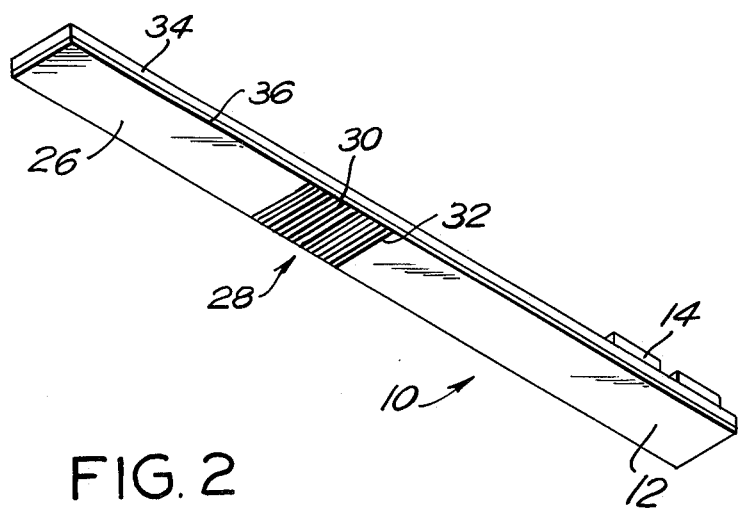
FIG. 2 is a test strip according to FIG. 1, seen obliquely from below.

FIG. 1 and FIG. 2 show a test strip indicated in its totality by the reference 10. The test strip 10 consists essentially of a test strip carrier 12 and one or more test fields, FIGS. 1 and 2 illustrate a test strip with two test fields 14.

The test fields 14 are present in the region of the front end 16 of the test strip carrier 12 which, in its totality, is formed longitudinally. On the opposite end, which is referred to as the rear end 18, there is provided a handling or holding region 20 which is bounded by the broken line 22.

The test fields are present on the upper side 24 of the test strip carrier, which is to be seen in FIG. 1. FIG. 2 shows the lower side 26 more clearly. A bar code can be seen which, in its totality, is indicated by the reference label 28. This bar code consists of individual code bars 30 of differing width running substantially transversely to the longitudinal direction of the test strip 10.

Preferably not only the breadth of the code bars but also their distances apart from one another are used for the desired batch-specific coding. In a practical embodiment, the code bars have a width of either 200 $\mu$m. or 400 $\mu$m., the narrow bars thereby representing a logical "0" and the wide code bars a logical "1". Two different distances between the code bars are correspondingly used. Furthermore, the code has a starting bar 32. The starting bar 32 or another appropriate part of the coding can also, at the same time, be used for the control of the correct positioning of the test strip 10 in an appropriate evaluation apparatus. A coding of the here described type, in which not only the breadth of the code bars 30 but also the breadth of the distances between the code bars is used for the coding, has an especially high information density but requires, on the other hand, an especially precise production of the bar code since otherwise even comparatively small errors in printing can lead to an erroneous reading thereof.

This high information density is necessary in order to be able to accommodate on the test strip the amount of information necessary for the batch-specific evaluation of at least about 50 bits. The usual test strips have a total length l (FIG. 1) of about 70 to 80 mm. This length has proved to be practical and represents a good compromise between optimum handling, relatively low production costs and sufficient bending strength of the test strip 10. Therefore, if possible, this length should not be exceeded.

Of the total length l, a partial length b is taken up by the test fields. If possible, this region should not be used for the application of the bar code for the following two reasons. On the one hand, it would be relatively difficult to read off a bar code 28, in an appropriate test strip evaluation device, applied to the lower side 26 of the test strip carrier 12 in the region of the test fields since an appropriately precise guiding of the test strip 10 is necessary for the reading of the bar code 28 which, in the region of the test fields 14, would be difficult to realize. On the other hand, the production of a test strip 10 with a bar code present under the test fields would also give rise to considerable problems. As already mentioned above, the test fields 14 should, if possible, be applied to the test strip carrier 12 before the properties of the test fields 14 are measured in order to determine the concentration-reflection dependency necessary for the evaluation, which is then applied to the test strip 10 in the form of a bar code 28. However, in the case of the application of the bar code 28, as is described in more detail in the following on the basis of the process according to the present invention, the use of pressure and possibly of an elevated temperature is necessary. If the bar code 28 were applied in the region of the test fields 14, then there would be a danger that the properties of the test fields 14 would change when applying the bar code 28 and thus would, in fact, no longer correspond to the actual relationships contained in the bar code 28.

If possible, the handling region 20 (length a in FIG. 1) should not be used for the bar code 28. In the case of relatively simple evaluation apparatus, for example, the test strip is to be introduced by hand into an appropriate reception opening and again to be capable of being removed therefrom. In this case, a part of the test strip 10 must, of necessity, project out of the apparatus. This part can then obviously not be used for the bar code. This problem does not exist in evaluation apparatus in which the test strips are introduced mechanically into the apparatus. However, even in this case, it is preferable not to use the handling region 20 for the bar code.

As can be seen from the above statements, the length available for the bar code 28 s=l−(a+b) is dependent upon the individual case. Starting from a practically realistic example in which the holding region has a length of a=30 mm. and the test field region has a length of b=15 mm. (including a small safety distance), then, in the case of a test strip length of l =75 mm., it follows that only about 30 mm. is available for the bar code.

If, furthermore, starting from a necessary information content of the bar code 28 of about 60 bits, then the information density is 20 bit/cm. Such a high information density is admittedly well known for conventional bar codes for other fields of use. However, in the case of the production of test strips, there are the special problems described hereinbefore due to which the experts in the field were clearly of the opinion that a bar code could not be used on test strips for providing the desired batch-specific information. This problem is overcome by the process according to the present invention described in more detail in the following.

For the here-described preferred process, it is, in the first place, important that the test strip carrier 12 is constructed from two layers which are preferably coextruded and bonded together. The upper layer 34 is preferably about 300 $\mu$m. thick and consists of a synthetic resin which has the necessary stiffness, polystyrene being preferred. The layer facing the lower side of the test strip 10 is very much thinner than the upper layer 34 and is preferably about 60 $\mu$m. thick and consists of a material upon which the code bars can be applied particularly well by the heat seal process described in the following. This material should have a relatively low softening point so that even in the case of relatively low temperatures and relatively low pressures, a dependable bonding is achieved with the dye layer forming the bar code 28, without too strong deformations being produced on the lower side 26 of the test strip carrier 12. For this purpose, polyethylene or ethylene vinyl acetate polymers have proved to be especially useful. Polyamide and acrylonitrile-butadienestyrene can also be used.

A preferred process according to the present invention is described in the following with reference to FIG. 3, this Figure merely showing the application of the bar code 28 by the preferred heat seal process, where the test strip carrier band 40 has already been previously bonded with the test field band 42.

Usually, test strips are produced in a manner such that onto a long band (e.g. 100 to 200 meters long) of test strip carrier material, the breadth of which corresponds to a whole-numbered multiple of the subsequent test strip length, there are applied one or more very much narrower bands 42 of test field material at the appropriate places and over the whole length. The breadth of the test field bands 42 corresponds to the subsequent length of the test fields on the finished test strips. This process step is usually carried out continuously, the test strip carrier band 40 and the test field band 42 thereby being drawn off from appropriate rolls and passed together through a device by means of which a connection is produced between both components. Thereafter (possibly after a drying or hardening phase), the total band consisting of test strip carrier band and the applied test field bands, which in the following is also called the test strip band 44, is cut up into pieces in a direction transverse to its longitudinal direction, the breadth of which corresponds to the breadth of the finished test strips. When the original test strip carrier band 40 corresponded in its breadth to the length of several test strips, then the total band, before cutting up in the transverse direction, is cut up in the longitudinal direction into several partial bands, the breadth of each of these partial bands corresponding to the length of a test strip. The bonding between the test strip carrier band and the test field band can be achieved in a large variety of different, known ways, for example by means of appropriate adhesion processes in which the materials used must be taken into account. This process step is not a part of the present invention and is well known so that it is here not necessary to describe it in detail.

It is important for the present invention that, in the case of the connecting of the test field band 42 to the test strip carrier band 40, the properties of the test field material with regard to the analysis to be carried out could possibly also change. This is one reason why it is especially preferred when there is first produced the connection between the test field band 42 and the test strip carrier band 40 and the total band 44 resulting therefrom is possibly temporarily stored, for example in the form of a roll, before the bar code for the batch-specific evaluation is determined and applied. From the roll with the total band there can easily be cut out several test strips which can be used as samples of the measurement of the reflection-concentration dependency of the particular batch. For the evaluation, it is advantageous to use apparatus which essentially also corresponds to the apparatus later used for the actual analysis in order to achieve conditions which are as realistic as possible.

If the desired reflection-concentration curve has been determined, then, with the help of an appropriate mathematical process, which is not the subject of the present invention, it can be represented in the form of a mathematical function which can be converted in known manner into a mechanically readable code. Furthermore, the code can contain further information, for example regarding the test to be carried out with the particular test strips.

Figure 3:
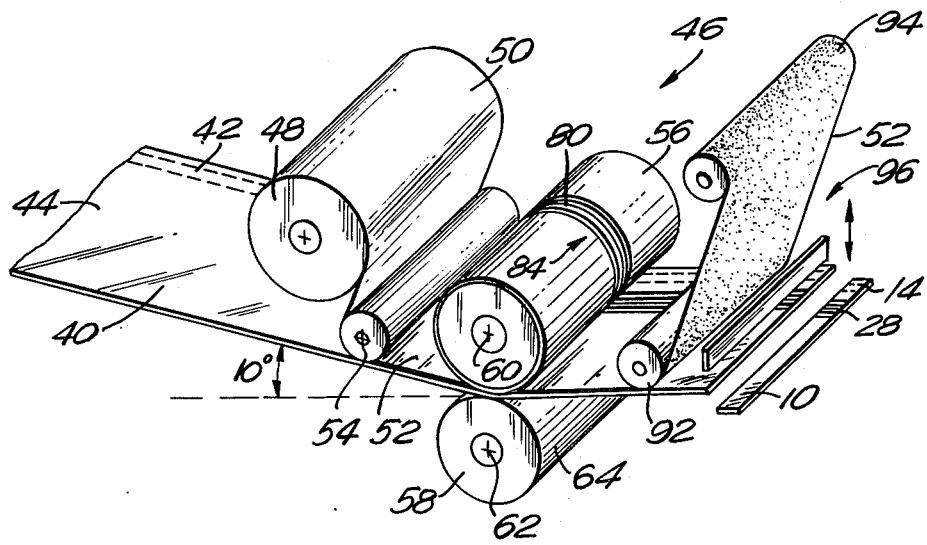
FIG. 3 is a highly schematic perspective illustration of a device for the application of a bar code to a band of a test strip carrier material.

FIG. 3 shows how this code is preferably applied to the total band 44 consisting of test strip carrier band 40 and test field band 42. The total band 44 runs at an angle of about 10° to the horizontal from a roll (not illustrated) into the code application device which, in its totality, is indicated by the reference 46. The test field band 42 is thereby present on the under side of the total band 44, which is not to be seen in the Figure and is, therefore, indicated by broken lines.

Above the in-running band 44 there is present a roll 48 with a heat seal film 50. The heat seal film consists essentially of an about 12 μm. thick polyester film upon which are a protective and separating lacquer, a dye layer necessary for the code bars and a sealing layer. The heat seal film 50 is rolled up on the roll 48 in such a manner that the polyester film 52 forming the dye layer carrier is on the outside of the roll 48.

The heat seal film passes from the roll 48 via a deflection roller 54 between a heat seal roller 56 and a pressure roller 58, which rotate about axes 60 and 62, respectively, both axes running parallel to the test strip band 44. The heat seal roller 56 is heated with the help of a (non-illustrated) internal heating mandrel. As is described in the following in more detail, it consists of a stainless steel hollow shaft and pushed-on pressure rings with associated fixing devices. The pressure roller 58 is made of steel, the surface 64 of which is highly polished.

The run-in angle of 10° is especially preferred for the process conditions described further below. In general, it is advantageous when the test band 44 runs around the heat-seal roller 56 to a small extent, i.e. the angle between the run-in direction and the run-off direction is 5° to 20°.

Figure 4:
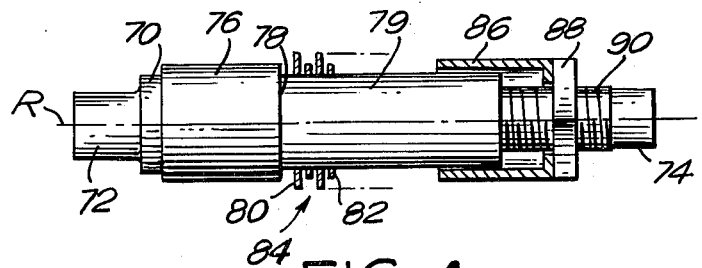
FIG. 4 is a cylindrical roller in cross-section for a device according to FIG. 4.

FIG. 4 shows a cross-section through a cylindrical roller preferably used for the process according to the present invention. As previously mentioned, the heating mandrel in the interior of the roller body 70 is not illustrated. The roller body 70 is preferably made in one piece and has, on both its ends, mounting axles 72 and 74 which can run in corresponding mountings on the machine. The axis of rotation is indicated by a chain line and is indicated by the label R. Adjacent the left-hand axle 72 in the Figure, the roller body 70 has a thickening 76 which, via an edge 78 vertical to the axis of rotation R, passes over into the ring receiver 79.

On the ring receiver 79, there sit in a succession, corresponding to the desired bar code, pressure rings 80 and intermediate rings 82 which, altogether, form a printing embossment 84. Depending upon the desired bar code, they are successively pushed onto the ring receiver 79 from the right-hand side of the Figure. In the case of the code example mentioned hereinbefore, pressure rings and intermediate rings of 200 μm. and 400 μm. thickness are used. However, the process according to the present invention has also proved to be useful for codings in which only 100 μm. wide bars (and consequently pressure rings 80) are employed.

The totality of the pressure rings 80 and intermediate rings 82 is pressed against the edge 78 by a pressing-on collar 86 with the help of an appropriate nut 88, which can be screwed on to a thread 90 and thereby fixed.

The cylindrical roller used for the printing on can, of course, also be constructed in another manner. However, the device here described is especially preferred because it represents a rapid and simple possibility of bringing on to test strip bands 44 the desired bar code 28 for a particular batch in the form of a corresponding printing embossment 84.

Figure 5A:
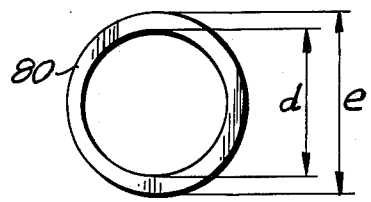
FIG. 5a and 5b are views of a pressure ring and of an intermediate ring, respectively, for a cylindrical roller according to FIG. 4.
Figure 5B:
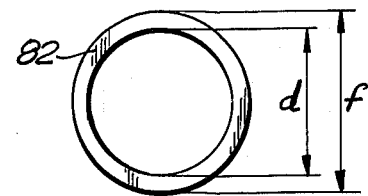

The differences in diameter between the pressure rings 80 and the intermediate rings 82 are shown greatly exaggerated in FIG. 4. The corresponding dimensions can be better appreciated from FIGS. 5a and 5b. The inner diameter of both types of rings d correspond to the outer diameter of the ring receiver 79 and, in a preferred example, are 48 mm. The outer diameter e of the pressure ring 80 is, in this example, 60 mm., whereas the outer diameter f of the intermediate ring 82 is 59 mm. The difference in radius of both types of rings is thus, in this case, only 0.5 mm. A construction of this type has proved to be useful in the case of the especially preferred heat seal process because the printing embossment 84 is, on the one hand, sufficiently deep in order to achieve a sharp printing and, on the other hand, even very thin pressure rings 80 still have the necessary rigidity and stability.

As is to be seen from FIGS. 3 and 4, the space occupied by the printing embossment 84 on the heat seal roller 56 accounts for only a comparatively small part of its breadth. Correspondingly, the rear side of the test strip band 44 is, for the reasons described further above, only printed in the relatively narrow region between the test fields 14 and 42 and the handing region 20.

Due to the applied pressure and the heating with the help of the heat seal roller 56, the dye layer on the dye layer carrier 52 is transferred to the test strip band 44 at the place and in each case in the breadth where a pressure ring 80 is present within the printing embossment 84. This transfer of a solid dye layer from a dye layer carrier is especially suitable for the coding of a test strip under the mentioned difficult conditions because the code bars are transferred precisely and sharply and no subsequent drying procedure is necessary.

The code bars are fixed by the melt adhesive present on the heat seal film 50 and are covered with the protective and separating lacquer also transferred from the dye layer carrier 52.

The dye layer carrier film 52 remaining over is wound up via a second deflection roller 92 onto a take-up roller 94. The test strip band 44 passes to a schematically illustrated cutting device 96, where it is cut up transversely to its direction of transport into individual test strips 10.

In the case of the here-illustrated preferred version of the process according to the present invention, the code bars 28 are transferred directly to the carrier as a dye layer, i.e. in the form of an extraordinarily thin film. Although this version is especially preferred because of its simplicity and the quality of the product achieved, in other cases of use it can be expedient first to print the bar code onto an appropriate band material and then to fix it, parallel to the test field band 42, onto the test strip carrier band 40. For this purpose, it is especially preferred to use a synthetic resin film which is first printed with the bar code and subsequently attached to the carrier band 40.

In the case of the example already mentioned above several times, in which the bar code consists of about 60 bits with 200 m. and 400 m. wide bars and distances, it has proved useful to operate with a surface temperature of the pressure rings 80 of about 130° C. and a feed rate of 4 meters/minute. The pressure force between the heat seal roller 56 and the pressure roller 58 is thereby about 400 Newton (N).

It will be appreciated that the instant specification and claims are set forth by way of illustration and not limitation, and that various modifications and changes may be made without departing from the spirit and scope of the present invention.

We claim:

1. A process for the production of an analysis test strip having an elongated carrier with at least one test field fixed thereon, the process comprising: providing a band of carrier material sufficient for a plurality of test strips; batchwise producing test field material in an amount sufficient for the plurality of test strips and obtaining batch specific information for the quantitative evaluation of said test field material; in a chronologically separate step, fixing the test field material in the form of at least one narrow band onto a parallel-running substantially wider band of carrier material having a longitudinal axis and two longitudinal edges; cutting the carrier band, with the test field material band fixed thereon, transversely to the longitudinal axis thereof and into a plurality of test strips; and, prior to the cutting step and after obtaining said batch-specific information, applying a bar code running parallel to the longitudinal edges of the carrier band including said batch-specific information.

2. The process according to claim 1, further comprising obtaining the batch-specific information after fixing the test field material onto the test strip carrier material.

3. The process according to claim 1 or 2, wherein the step of applying the bar code comprises transporting the band in one direction, applying the bar code directly onto the running carrier band between and through a cylindrical roller and a pressure device by rotating the pressure device and the cylindrical roller about an axis parallel to the band surface and transversely to the direction of transport of the band.

4. The process according to claim 3, wherein the step of applying the bar code further comprises forming the desired bar code prior to passing the carrier band between the roller and pressure device with a plurality of pressure rings and intermediate rings of different breadth by applying same concentrically to a common axis on the roller with the breadth and order of succession thereof corresponding to the desired bar code.

5. The process according to claim 3, wherein the step of applying the bar code further comprises providing a dye layer on a dye layer carrier band and running the dye layer carrier band through the cylindrical roller and the pressure device between the test strip carrier band and the cylindrical roller.

6. The process according to claim 5, further comprising forming the dye layer carrier band from a synthetic resin film and applying a layer of separating lacquer, a dye layer and a layer of heat seal agent thereon and wherein the cylindrical roller is heated to transfer the dye layer to the test strip carrier in conjunction with the pressure of the cylindrical roller.

7. The process according to claim 1, wherein the bar code is applied to the surface of the carrier band opposite from that carrying the test field and spaced apart therefrom.

8. The process according to claim 1, wherein the bar code essentially comprises two different widths of code bars and is applied with an information capacity of at least 30 bits, and the width of the smaller bars is not more than 400 $\mu$m.

9. The process according to claim 1, wherein the bar code essentially comprises two different widths of code bars and is applied with an information capacity of at least 50 bits an the width of the smaller code bars is not more than about 200 $\mu$m.

* * * * *